US00PP31966P3

(12) United States Plant Patent
Olesen et al.

(10) Patent No.: US PP31,966 P3
(45) Date of Patent: Jul. 14, 2020

(54) ***CLEMATIS* PLANT NAMED 'EVIPO094'**

(50) Latin Name: *Clematis integrifolia*
Varietal Denomination: Evipo094

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,901

(22) Filed: Sep. 10, 2018

(65) Prior Publication Data

US 2020/0084938 P1 Mar. 12, 2020

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

(56) References Cited

PUBLICATIONS

UPOV hit on *Clematis* plant named 'Evipo094', QZ PBR 20172274, filed Sep. 19, 2017.*
http://www.poulsenroser.com/assortment/rose-collections/paillette/fenfang.aspx, downloaded Jun. 20, 2019.*

* cited by examiner

*Primary Examiner* — Anne Marie Grunberg

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis*.
Species: *integrifolia*.
Variety denomination: 'Evipo094'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 1994 and the resulting seeds were planted the following winter in a controlled environment in Guernsey, Channel Islands, United Kingdom. The new variety named 'Evipo094' originated as a single seedling from the stated cross.

The new *clematis* plant may be distinguished from its female seed parent and male pollen parent by the following characteristics. The female seed parent has violet blue flowers, while the new variety has red-purple flowers. The male seed parent has violet blue tepals while the new variety has red-purple tepals.

The objective of the hybridization of this *clematis* plant was to create a new and distinct variety for nursery culture with unique qualities such as:

1. Uniform and abundant red-purple flowers;
2. Vigorous and compact growth, making the variety suitable for container culture; and 3. Improved disease resistance.

This combination of qualities was lacking in *clematis* plants that were in commercial cultivation and the qualities have been substantially achieved in the new variety.

'Evipo094' was selected by Mogens N. Olesen and Raymond J. Evison in their *clematis* development program in the Channel Islands, United Kingdom in 1995. Asexual reproduction of 'Evipo094' by means of vegetative cuttings and traditional layering was first performed by Mogens N. Olesen and Raymond J. Evison in the nursery during the summer of 1995. This initial and subsequent asexual propagations have demonstrated that the characteristics of 'Evipo094' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo094'.

Specifically illustrated in FIG. 1 of the drawings are an open flower and tepals detached showing reproductive flower parts.

DETAILED DESCRIPTION OF THE VARIETY

Figure 1:
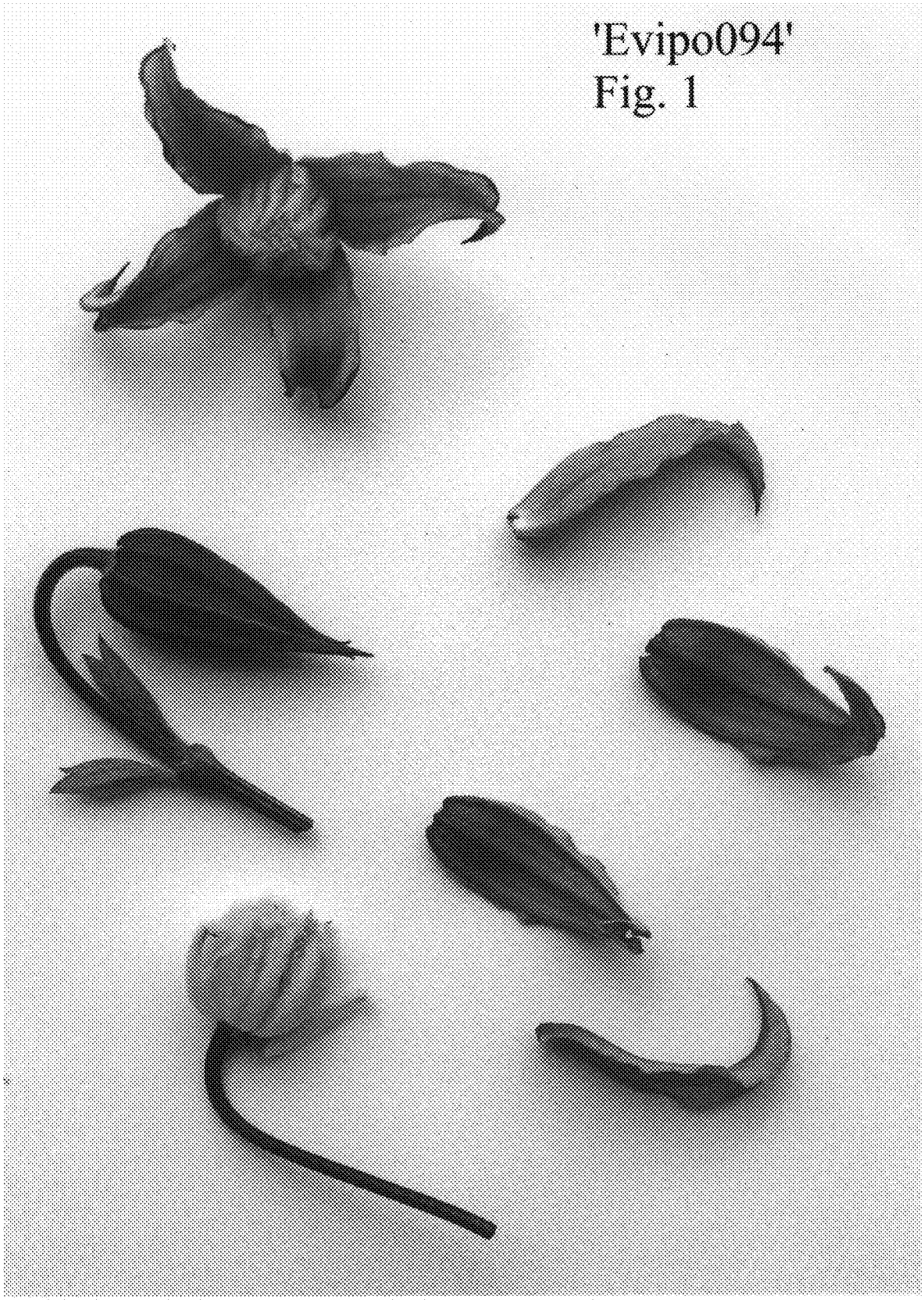
Figure 2:
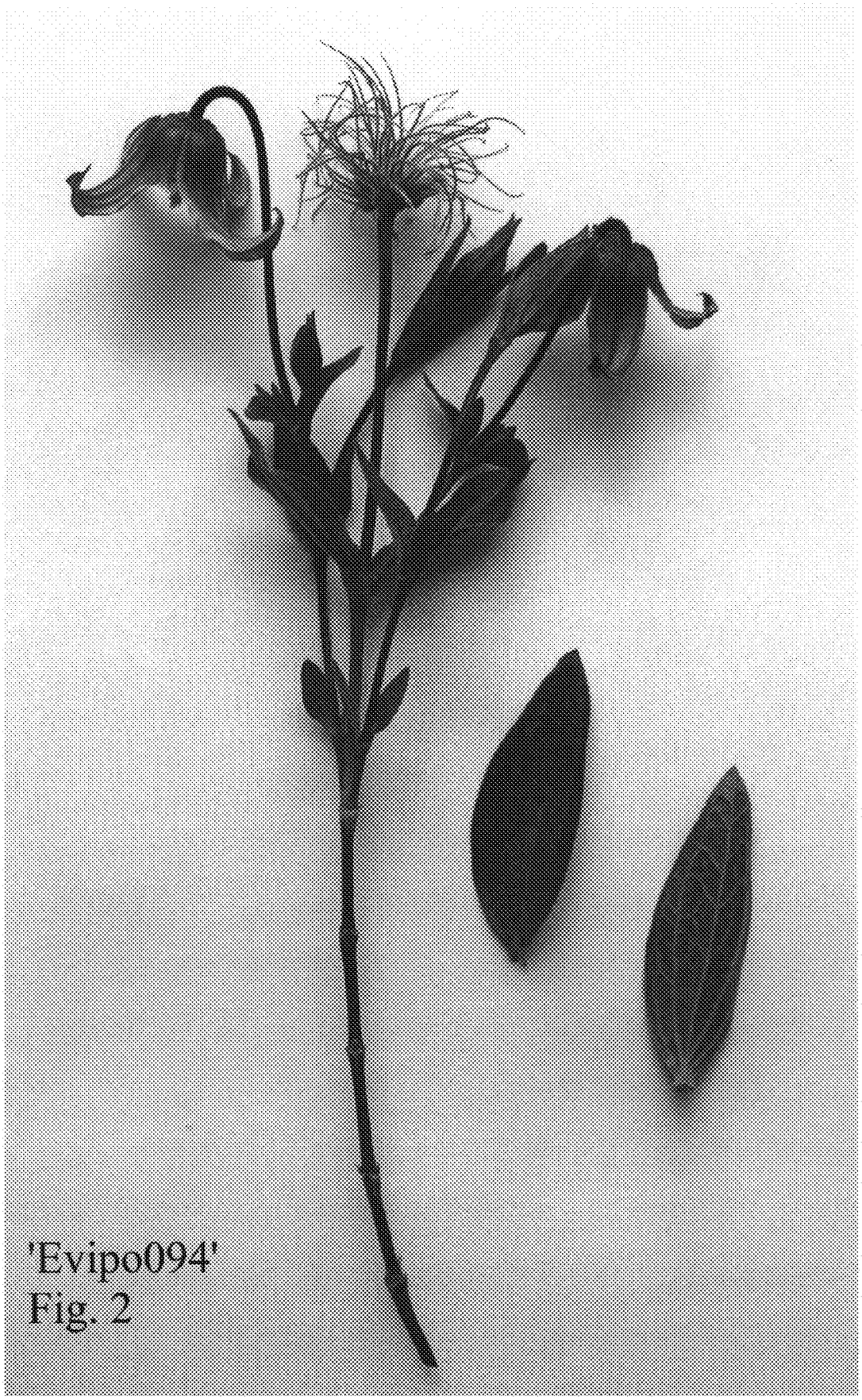
FIG. 2 shows a flowering branch, bare stem, and leaves. Illustrated plants are 2 years of age.

The following is a detailed description of 'Evipo094', as observed in its growth throughout the flowering period in Marion County Oreg. Observed plants were cultivated for a period of 24 months in a field nursery. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Stand by Me' described and illustrated in U.S. Plant Pat. No. 30,556 dated Jun. 4, 2019 are compared to 'Evipo094' in Chart 1.

CHART 1

| | 'Evipo094' | 'Stand by Me' |
|---|---|---|
| Height of plant | 35 to 40 cm | 98 cm |
| Tepal upper surface after opening | Purple-Violet Group N81B | Adaxial center nearest RHS 90A, adaxial margin between outer main vein and margin between RHS 90D and RHS 91A; abaxial center between RHS N92D and RHS 93A, margin between outer main vein and margin between RHS 93C and RHS 93D |
| Tepal Length | 36 mm | 33 mm |

FLOWER AND FLOWER BUD

Blooming habit: Recurrent. The natural flowering period is generally from May to September.

Flower bud:
- *Size*.—Normally 31 mm in length. Bud diameter is 12 mm.
- *Bud form*.—Long campanulate, broad based.
- *Bud color*.—Purple Group N79C.
- *Texture*.—Pubescent.

Pedicel:
- *Surface texture*.—Ribbed.
- *Length*.—35 to 50 mm in length with 3 mm diameter.
- *Color*.—Greyed-Purple Group N187A.
- *Strength*.—Moderately strong.

Receptacle:
- *Surface texture*.—Lightly pubescent.
- *Shape*.—Broad funnel.
- *Size*.—1 mm (h)×3 mm (w).
- *Color*.—Yellow-Green Group 144A with intonations of Greyed-Purple Group N187A.

Peduncles:
- *Size*.—30 to 85 mm long, by 2 mm wide.
- *Color*.—Yellow-Green Group 145A and Greyed-Purple Group N187A.

Flower arrangement:
- *Location on vine*.—New growth only.
- *Borne*.—Singly or in clusters of 3 to 7 per flowering branch.

Flower bloom:
- *Size*.—On average, flowers are 50 mm in diameter and 30 mm in depth.
- *Profile*.—Open flowers are nodding, urceolate.
- *Fragrance*.—None.
- *Lasting quality*.—Flowers normally remain up to 15 days on the plant.

Tepals:
- *Tepal color*.—The upper surface is Purple-Violet Group N81B. The lower surface is Purple-Violet Group N81A with intonations of Purple Group N79B.
- *Texture*.—Rugose.
- *Quantity*.—Normally 4 tepals.
- *Size*.—36 mm in length by 12 mm wide.
- *Shape*.—Individual tepal shape is ovate. The tepal apex is acute. The tepal base is flat.
- *Apex recurvature*.—Recurved strongly.
- *Tepal cross section*.—Flat.
- *Margins*.—Entire. Strong undulations.
- *Persistence*.—Tepals drop off cleanly.

Reproductive organs:
- *Pollen*.—None observed.
- *Anthers*.—Size: 3 mm in length. Color: Yellow Group 5D. Quantity: On average, 35.
- *Filaments*.—Color: Yellow Group 4D. Length: 5 mm. Texture: Pubescent.
- *Pistils*.—Quantity: On average, 15.
- *Stigmas*.—Level in location relative to the length of the filaments and the height of the anthers.
- *Styles*.—Color: Yellow-Green Group 150D. Length: 15 mm.

Seed head characteristics: Seed not observed to date.
- *Size*.—The entire seed cluster is 45 mm in height by 40 mm in diameter. Individual seeds have a plume which is 35 mm long by 1 mm wide.
- *Color*.—Greyed-White 156D.
- *Quantity of seed*.—80 average.
- *Style appearance*.—Plumose, semi-erect.

PLANT

Plant form: Upright.

Plant growth: Moderately vigorous.

Size: Seasons growth attains 35 to 40 cm in height. Average spread is 40 cm.

Stems:
- *Color*.—Juvenile stems are Yellow-Green Group 144B with intonations of Greyed-Red Group 181A. Mature stems are Greyed-Orange Group 177A.
- *Internodes*.—On average, 20 cm between nodes.
- *Length*.—Normally 12 to 18 cm from the base of the plant to the flowering portion of the stem.
- *Diameter*.—About 3 mm.
- *Texture*.—Mature stems are ribbed.

Plant foliage:
- *Leaf characteristics*.—Deciduous.
- *Arrangement*.—Opposite, simple, sessile.
- *Leaf size*.—About 75 mm (l)×28 mm (w).
- *Leaf color*.—Juvenile upper Yellow-Green Group 146A with intonations of Greyed-Purple Group 183B. Juvenile lower Yellow-Green Group 146A with intonations of Greyed-Purple Group 183B. Mature upper Yellow-Green Group 146A. Mature lower Yellow-Green Group 146A.
- *Leaf texture*.—Upper surface is smooth, lower surface is rugose.
- *Stipules*.—Absent.
- *Petioles*.—None.
- *Leaflet shape*.—Elliptic. The base is acute and the apex is acute.

*Margin*.—Entire.
*Thickness*.—Moderate.
*Glossiness*.—Glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo094', substantially as described and illustrated, due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo094'

'Evipo094'